United States Patent [19]

Schulz et al.

[11] 4,234,743

[45] Nov. 18, 1980

[54] ISOMERIC DIAMINOBENZOPHENONEDICARBOXYLIC ACIDS AND METHOD FOR PREPARING SAME

[75] Inventors: Johann G. Schulz, Pittsburgh; Anatoli Onopchenko, Monroeville; Edward T. Sabourin, Allison Park, all of Pa.

[73] Assignee: GR & DC, Pittsburgh, Pa.

[21] Appl. No.: 39,868

[22] Filed: May 17, 1979

[51] Int. Cl.³ .............................................. C07C 101/68
[52] U.S. Cl. ..................................................... 562/457
[58] Field of Search ................................ 562/457, 458

[56] References Cited

U.S. PATENT DOCUMENTS 2,653,971   9/1953   Balch ..................................... 562/458

FOREIGN PATENT DOCUMENTS 289108   of 0000   Fed. Rep. of Germany .
2328757   1/1975   Fed. Rep. of Germany ........... 562/458
1436810   5/1976   Fed. Rep. of Germany ........... 562/458

OTHER PUBLICATIONS

Morrison et al., Organic Chem., p. 916 (1966).

*Primary Examiner*—Natalie Trousof
*Assistant Examiner*—James H. Reamer

[57] ABSTRACT

3,3'-diamino-4,4'-benzophenonedicarboxylic acid, 4,4'-diamino-3,3'-benzophenonedicarboxylic acid and 3,4'-diamino-3',4-benzophenonedicarboxylic acid and process for preparing same.

3 Claims, No Drawings

ISOMERIC DIAMINOBENZOPHENONEDICARBOXYLIC ACIDS AND METHOD FOR PREPARING SAME

BACKGROUND OF THE INVENTION

1. Field of the Invention

This invention is directed to 3,3'-diamino-4,4'-benzophenonedicarboxylic acid, 4,4'-diamino-3,3'-benzophenonedicarboxylic acid and 3,4'-diamino-3',4-benzophenonedicarboxylic acid and process for preparing same.

2. Description of the Prior Art

In German Pat. No. 289,108 a process for preparing 4,4'-diamino-3,3'-benzophenonedicarboxylic acid is disclosed which comprises (1) condensing anthranillic acid (o-aminobenzoic acid) with formaldehyde to obtain dianalinodiphenylmethane dicarboxylic acid [N,N'-di(2-carboxyphenyl)diaminomethane], (2) rearrangement of the latter in the presence of hydrochloric acid to obtain 4,4'-diamino-3,3'-diphenylmethane dicarboxylic acid and (3) oxidizing 4,4'-diamino-3,3'-diphenylmethane dicarboxylic acid with sulfur to obtain the desired 4,4'-diamino-3,3'-benzophenonedicarboxylic acid. Even though anthranilic acid is commercially available, unfortunately the patented process requires several reaction steps, including a rather tedious oxidation step involving sulfur-containing reagents, leading to the production of odor-causing species requiring extensive purification treatments.

SUMMARY OF THE INVENTION

We have discovered a simple novel process utilizing readily-available materials which will produce a novel mixture containing not only the desired 4,4'-diamino-3,3'-benzophenonedicarboxylic acid but also two novel isomers thereof, namely 3,3'-diamino-4,4'-benzophenonedicarboxylic acid and 3,4'-diamino-3',4-benzophenonedicarboxylic acid.

In carrying out the process, 3,4,3',4'-benzophenonetetracarboxylic dianhydride (BTDA) is reacted with aqueous ammonia to obtain the corresponding ammonium salt of diamidobenzophenonedicarboxylic acid. The ammonium salt so obtained in the presence of a base, such as sodium hydroxide or potassium hydroxide, will react with additional BTDA to form the corresponding sodium salt of the diamidobenzophenonedicarboxylic acid and water. The same intermediate can also be obtained from the reaction of BTDA with dry ammonia at elevated temperatures to produce the corresponding diimide which on treatment with caustic will produce the salt diamidobenzophenonedicarboxylic acid. The sodium salt is then subjected to reaction with an alkali metal hypohalite, such as sodium hypochlorite or potassium and a base, such as sodium hydroxide or potassium hypochlorite, and a base, such as sodium hydroxide or potassium hydroxide, in accordance with the Hofmann reaction (see, for example, *Organic Reactions,* Volume III, Roger Adams, Editor in Chief, John Wiley and Sons, N.Y., N.Y., Chapter 7, pages 267–306), to obtain an isomeric mixture of the sodium salts of diaminobenzophenonedicarboxylic acids plus an alkali metal halide and an alkali metal carbonate. The mixture is then treated with an acid, such as sulfuric acid, hydrochloric acid, phosphoric acid, etc., to obtain the desired mixture of diaminobenzophenonedicarboxylic acids as a precipitate. Simple filtration is all that is required to obtain the desired mixture of acids, namely, 3,3'-diamino-4,4'-benzophenonedicarboxylic acid, 4,4'-diamino-3,3'-benzophenonedicarboxylic acid and 3,4'-diamino-3',4-benzophenonedicarboxylic acid.

The individual acids can be recovered from the latter mixture in any convenient or suitable manner. Thus the mixture can be subjected to extraction with hot (50° to 110° C.) hydrochloric acid until no further solubilization occurs. The acid extract can then be cooled to room temperature (26° C.) and diluted with water, resulting in the precipitation of solids. After filtration the recovered solids are washed with water and dried in a vacuum oven for about 0.5 to about six hours at a temperature of about 50° to about 200° C. to produce the isomer 4,4'-diamino-3,3'-benzophenonedicarboxylic acid. The hydrochloric acid insoluble portion of the product contains the two novel isomers, namely, 3,3'-diamino-4,4'-benzophenonedicarboxylic acid and 3,4'-diamino-3',4-benzophenonedicarboxylic acid. These isomers can be separated from each other, if desired, by conventional extraction procedures using organic solvents, such as tetrahydrofuran, p-dioxane, 1-methylpyrrolidinone, etc., since the solubility of the symmetrical 3,3'-diamino-4,4'-benzophenonedicarboxylic acid is different from the solubility of the unsymmetrical 3,4'-diamino-3',4-benzophenonedicarboxylic acid.

The reactions described above are easily effected requiring only amounts of reactants stoichiometrically needed therefor. The reaction parameters are not critical. Thus the temperatures can be in the range of about −20° to about 80° C., preferably about −10° to about 26° C. and at atmospheric pressure and the reaction times in the range of about 30 minutes to about 10 hours, preferably about one to about four hours.

The reactions described above can further be illustrated by the following series of equations:

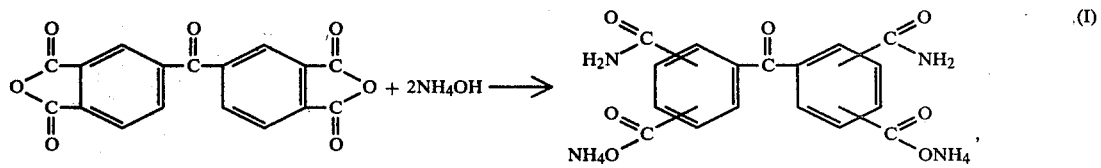

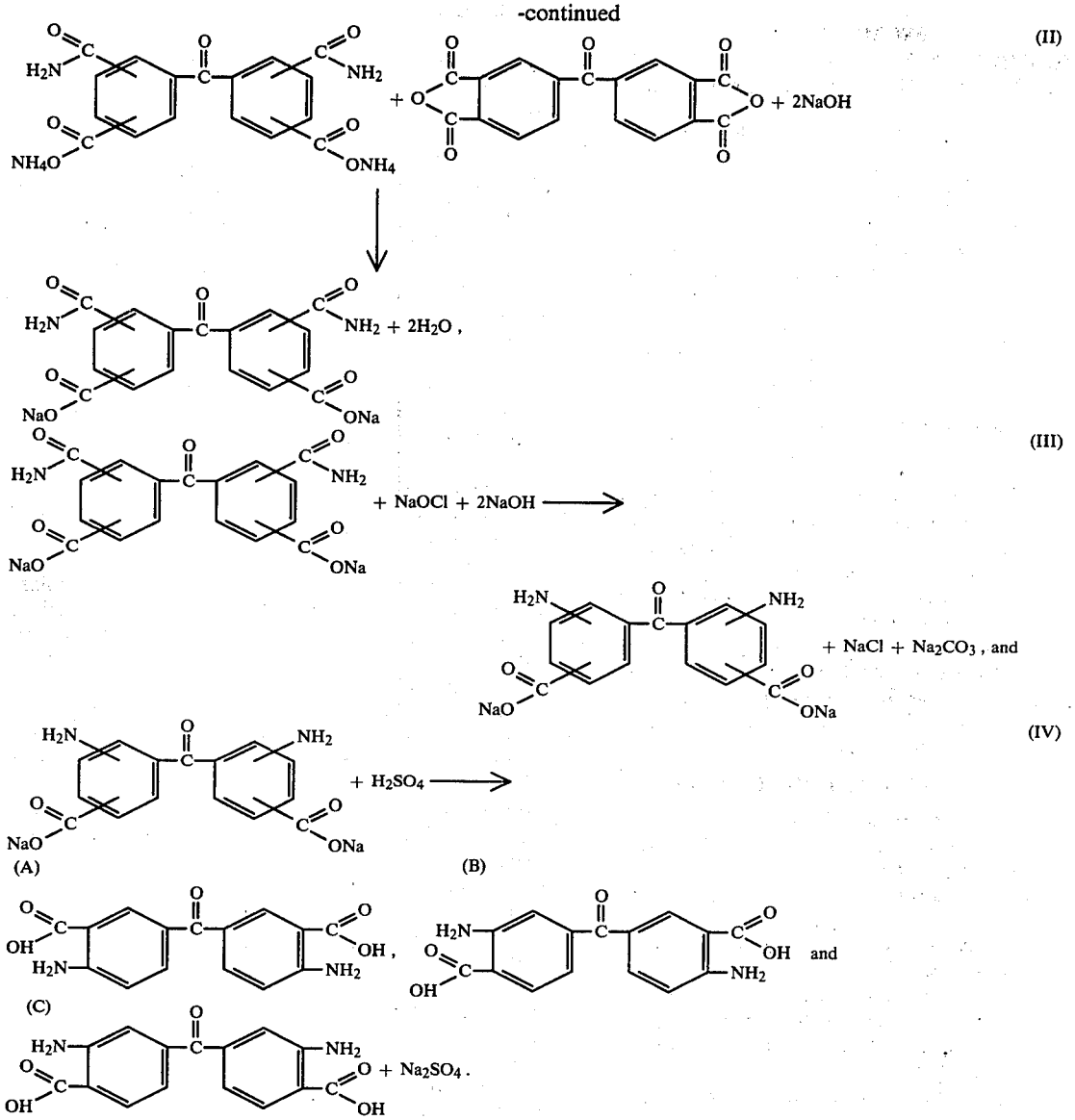

In each of the above formulae wherein some substituents have been assigned no specific positions on the rings, it is understood that the positions are solely in the 3,3', 4 and 4' positions.

DESCRIPTION OF PREFERRED EMBODIMENTS

EXAMPLE I

A solution of sodium benzophenone diamidocarboxylate was prepared by adding 125 grams of concentrated ammonium hydroxide to 80.5 grams of BTDA in 100 milliliters of water, stirring until solution occurred, followed by addition of a second 80.5 gram portion of BTDA, 50 milliliters of water and 80 grams of 50 percent aqueous sodium hydroxide solution, stirring until solution was complete and then filtering. An aqueous sodium hypochlorite-sodium hydroxide solution was prepared by bubbling 85.2 grams of chlorine into a solution containing 192 grams of sodium hydroxide dissolved in 768 grams of water while maintaining a temperature between −20° and 10° C. The aqueous sodium hypochlorite-sodium chloride solution was brought to −10° C. and then, while stirring, introduced into a three-liter, two-necked, round-bottom flask, equipped with a stirrer, a reflux condenser and an addition funnel. The sodium benzophenone diamidodicarboxylate solution previously prepared was added dropwise to the aqueous sodium hypochloritesodium hydroxide solution while maintaining the temperature between −10° and 10° C. After addition was completed, the reaction mixture was permitted to come to room temperature (26° C.) and then heated to 90° C. over a one-hour period. The solution was cooled to 60° C. and sufficient concentrated hydrochloric acid was added thereto until a pH of 7.5 was obtained. The reaction mixture was then treated with 25 grams of sodium bisulfite in 100 milliliters of water and 20 grams of activated charcoal. After stirring for five minutes and filtering, the filtrate was acidified with hydrochloric acid to a pH of 4.5 The precipitated solids were filtered, washed several times with water and dried in a vacuum oven at 95° C. over a period of 12 hours to obtain 90 grams of a product having a neutral equivalent of 192. A portion of this product was redissolved in sodium hydroxide, filtered to remove a small amount of insoluble material and the filtrate then sprung with hydrochloric acid. The precipitated solids were filtered under suction, washed with water and dried in a vacuum oven at 95° C. arbitrarily for 12 hours, resulting in yellow-green solids having a neutral equivalent of 150, corresponding to an isomeric mixture of the following diaminobenzophenonedicarboxylic acids: 3,3'-diamino-4,4'-benzophenonedicarboxylic acid, 4,4'-diamino-3,3'-benzophenonedicarboxylic acid and 3,4'-diamino-3',4-benzophenonedicarboxylic acid. The theoretical neutral equivalent of this mixture is 150. The product did not melt, but showed signs of decomposition, accompanied by evolution of gas, in the temperature range of 285°-290° C.

EXAMPLE II

A run similar to Example I was carried out wherein 98 grams of yellow-greenish product was isolated as in Example I. This product was extracted four times with hot concentrated hydrochloric acid using 300 milliliter portions, at which point only traces of the remaining material appeared to dissolve in the acid. The acid extracts were cooled to room temperature and diluted with two volumes of water, resulting in the precipitation of tan solids. After filtration, the material was dried in a vacuum oven over a twelve-hour period to give 61.1 grams of product. This material decomposed with evolution of gas at about 300° C. rather than melting. A neutral equivalent value of 148 was obtained, which was in good agreement with the theoretical value of 150 for the expected compound, 4,4'-diamino-3,3'-benzophenonedicarboxylic acid. Analysis by gas liquid chromatography on a 20-inch column, UCW982, programmed from 200° to 300° C. at 8°/minute gave a single peak as the trimethylsilyl derivative obtained by reaction of bis-trimethylsilylacetamide with the acid. The NMR spectrum in dimethylsulfoxide-$d_6$ showed six aromatic ring hydrogens and six exchangeable hydrogens for the $NH_2$ and COOH functionalities. The aromatic protons were distributed in an AB pattern, $\delta A = 7.1$ ppm, $\delta B = 7.9$ ppm, with coupling constants $J_{AB} = 9.5$ cycles per second; the portion of the AB peak at 7.9 was further split by a 2 cps meta coupling; and the remaining portion at 8.2 ppm also showed the 2-cps meta-coupling. The solubility data, decomposition point, neutral equivalent value and the NMR spectrum are consistent with the product being 4,4'-diamino-3,3'-benzophenonedicarboxylic acid

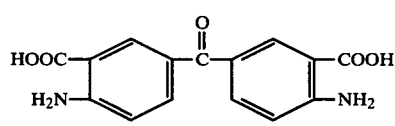

The hydrochloric acid-insoluble portion of the product was washed with water and then dried. The resulting greenish-yellow solid, amounting to 35 grams, melted with decomposition at 250°-260° C. and gave a neutral equivalent value of 151 which was in good agreement with the theoretical value of the expected compounds, 3,3'-diamino-4,4'-benzophenonedicarboxylic acid and 3,4'-diamino-3',4-benzophenonedicarboxylic acid. Unfortunately, the trimethylsilyl derivative of this portion of product was not stable to gas chromatographic analysis, so that exact distribution of the two isomers could not be determined. However, from the NMR spectrum integrals, it is possible to estimate the amounts of the remaining two isomers, namely, 3,3'-diamino-4,4'-benzophenonedicarboxylic acid:

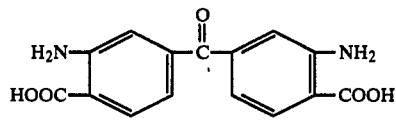

and 3,4'-diamino-3', 4-benzophenonedicarboxylic acid:

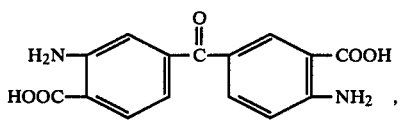

to the extent of about ±5 percent. Using this estimate, 71 percent of the hydrochloric acid-insoluble product is 3,4'-diamino-3',4-benzophenonedicarboxylic acid and 29 percent is 3,3'-diamino-4,4'-benzophenonedicarboxylic acid. This means that the percentages of the three isomers, 4,4'-diamino-3,3'-benzophenonedicarboxylic acid, 3,4'-diamino-3',4-benzophenonedicarboxylic acid and 3,3'-diamino-4,4'-benzophenonedicarboxylic acid as prepared in Example I and this Example II are 63, 26 and 11 percent, respectively. This indicates, unexpectedly, that in the rearrangement of the substituents in the 3,3',4 and 4' positions on the BTDA intermediates the loss of the carboxyl group in position 4 as compared to position 3 is favored by a factor of 3.

The above is most unusual. When BTDA is subjected to the Hofmann reaction it would be expected that one of the 3,3',4,4'-positions would be occupied by a carboxyl group and an adjacent position by an amino group, resulting in three diaminobenzophenonedicarboxylic acid isomers, namely, 3,3'-diamino-4,4'-benzophenonedicarboxylic acid, 4,4'-diamino-3,3'-benzophenonedicarboxylic acid and 3,4'-diamino-3',4-benzophenonedicarboxylic acid. One would additionally expect, on a statistical basis and in the absence of other information, to find the resulting mixture to contain approximately one-third of each of the three isomers. However, on pages 294 and 295 of *Organic Reactions*, referred to above, an example is given wherein 4-nitrophthalamide

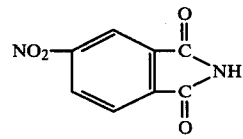

is subjected to the Hofmann reaction, resulting in the production of a mixture, representing a 70 percent yield of 4-nitroanthranlic acid,

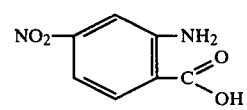

and a 20 percent yield of 3-nitroanthranilic acid,

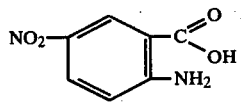

This shows that an electron-withdrawing group, or deactivating group, such as the nitro group in the 4-position influences the Hofmann reaction so that upon rearrangement the amino group winds up in the meta position relative to the nitro group. Since the phenyl ketone group in BTDA, namely

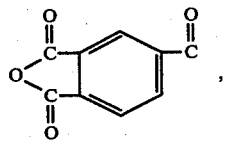

is also an electron-withdrawing group, or deactivating group, one would except similar result when BTDA is subjected to the Hofmann reaction. This would then lead one to expect the presence predominantly of the 3,3'-diamino isomer. Instead, we have obtained only 11 percent of the 3,3'-diamino isomer and unexpectedly 63 percent of the 4,4'-diamino isomer.

In addition to the above, it would be expected that subjecting BTDA to the Hofmann reaction would lead to complications, since the carbonyl group would have a tendency towards Shiff base formation with the amine product, one of the most characteristic reactions of ketones known, as well as possible cyclic ring formations. The ketone group in BTDA would also be expected to serve as a weak link for the halogen atom, or halogen-containing species, such as the hypochlorite ion, to attack, leading to the introduction of halogen at the bridge as well as fragmentation through oxidation. Most unexpectedly, high yields of Hofmann product were obtained in spite of a report that with aromatic amides hydrolysis prior to rearrangement may occur to such an extent that the yield is seriously lowered (p. 280, *Organic Reactions*, Volume III, cited earlier).

The difunctional isomeric mixture of diaminobenzophenonedicarboxylic acids, or any of the specific isomers thereof, can be used in the preparation of polymers. In a specific example therefor 39 parts by weight of the isomeric mixture prepared in Example II was mixed with 100 parts by weight of EPON-828, a commercial epoxy resin, and the resulting mixture was heated at atmospheric pressure to 120° C. over a period of 1.2 hours, resulting, on cooling, in a hardened, crosslinked resin. A barcol hardness value of 25 was obtained on a Barcol Impressor 934-1, indicating that a crosslinked epoxy resin was formed suitable for use as a coating for metals, wires, etc.

Obviously, many modifications and variations of the invention, as hereinabove set forth, can be made without departing from the spirit and scope thereof, and, therefore, only such limitations should be imposed as are indicated in the appended claims.

We claim:
1. A novel isomeric mixture containing 3,3'-diamino-4,4'-benzophenonedicarboxylic acid, 4,4'-diamino-3,3'-benzophenonedicarboxylic acid and 3,4'-diamono-3',4-benzophenonedicarboxylic acid.
2. As a new compound 3,3'-diamono-4,4'-benzophenonedicarboxylic acid.
3. As a new compound 3,4'-diamino-3',4-benzophenonedicarboxylic acid.

* * * * *